United States Patent [19]

Ogawa et al.

[11] Patent Number: 5,530,494

[45] Date of Patent: Jun. 25, 1996

[54] OPTHALMIC PHOTOGRAPHING APPARATUS HAVING PHOTOGRAPHIC LIGHT AMOUNT CORRECTION INPUT MEANS

[75] Inventors: Tetsuji Ogawa, Inagi; Takeshi Kitamura, Kawasaki, both of Japan

[73] Assignee: Canon Kabushiki Kaisha, Tokyo, Japan

[21] Appl. No.: 504,786

[22] Filed: Jul. 20, 1995

[30] Foreign Application Priority Data

Jul. 25, 1994 [JP] Japan .................................. 6-192940

[51] Int. Cl.$^6$ ........................................................ A61B 3/14
[52] U.S. Cl. ............................................. 351/206; 354/62
[58] Field of Search ............................ 351/205, 206–210; 354/62

[56] References Cited

U.S. PATENT DOCUMENTS 4,786,162 11/1988 Fujiwara et al. ...................... 351/206

Primary Examiner—William L. Sikes
Assistant Examiner—Huy Mai
Attorney, Agent, or Firm—Fitzpatrick, Cella, Harper & Scinto

[57] ABSTRACT

An ophthalmic photographing apparatus has photographing device for directing the image of an eye to be examined obtained by illuminating the eye to be examined with a predetermined photographing light amount to a recording medium or an image pickup element, a detector for detecting information about the kind and/or sensitivity of the recording medium or the image pickup element into which the image of the eye to be examined is introduced, a photographing light amount correction input device for inputting the correction condition of a photographing light amount, and controller for varying at least one of the correction width and the correction stage of the photographing light amount correction condition inputted by the photographing light amount correction input device on the basis of the result of the detection by the detector. With at least one of the correction width and the correction stage set by the control means, the photographing light amount by the photographing device is controlled on the basis of the input correction condition by the photographing light amount correction input device.

6 Claims, 2 Drawing Sheets

OPTHALMIC PHOTOGRAPHING APPARATUS HAVING PHOTOGRAPHIC LIGHT AMOUNT CORRECTION INPUT MEANS

BACKGROUND OF THE INVENTION

1. Field of the Invention

This invention relates to an ophthalmic photographing apparatus having the function of correcting the photographing light amount.

2. Related Background Art

There is known an ophthalmic photographing apparatus which can select film or a television camera as a recording medium or an image pickup element for imprinting the image of the fundus of an eye to be examined and can set a proper photographing light amount conforming to the recording medium during photographing.

Also, in a retinal camera, the reflectance of the fundus of an eye which is an object to be photographed differs greatly from one examinee to another and further, there is included in the eye a portion such as Macula or Disk of which the reflectance differs as much as several times to several tens of times from an ordinary region and therefore, in the case of a low reflectance like that of a lesion portion, it is necessary to effect the fine correction of the photographing light amount conforming thereto. There is also known an ophthalmic photographing apparatus having the function of effecting such correction of the photographing light amount.

Also, by combining a light amount conforming to a recording medium and the light amount correcting function, it becomes possible to effect photographing always at the appropriate exposure amount in spite of any variation in the recording medium and any variation in the reflectance of the fundus of the eye. As such light amount correcting function, there is known one having a predetermined light amount correction width and a predetermined photographing light amount correction stage.

However, the light amount correcting function of the above-described example of the prior art has only a variation in the photographing light amount as the standard and does not take into account the γ characteristic of the recording medium and the difference in the dynamic range, and this gives rise to the problem that even if the photographing light amount correction width and the photographing light amount correction stage are optimum for a certain recording medium, the photographing light amount correction width is too rough or the photographing light amount correction stage is unsuitable for another recording medium and therefore the photographing operation becomes difficult and the original light amount correcting function cannot be achieved.

SUMMARY OF THE INVENTION

It is a first object of the present invention to solve the above-noted problem and to provide an ophthalmic photographing apparatus in which an optimum exposure amount is obtained irrespective of the kinds of recording media used.

It is a second object of the present invention to provide an ophthalmic photographing apparatus which has photographing light amount correction input means conforming to the kind of a recording medium used and which is excellent in operability.

Other objects of the present invention will become apparent from the following detailed description of an embodiment of the invention.

DESCRIPTION OF THE PREFERRED EMBODIMENTS

Figure 1:
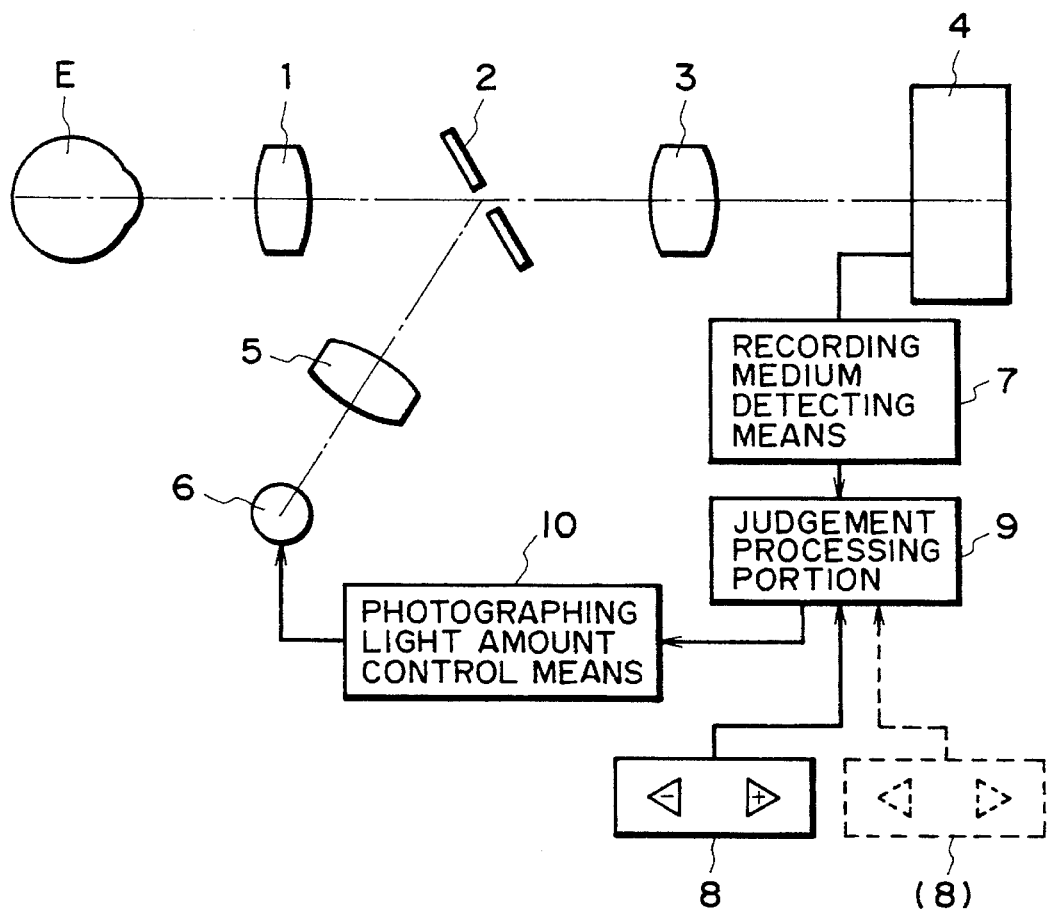
FIG. 1 is a block diagram showing the construction of an embodiment of the present invention.

The present invention will hereinafter be described in detail with respect to an embodiment thereof shown in the drawings.

Referring to FIG. 1 which shows the construction of the present embodiment applied to a retinal camera, an objective lens 1, an apertured mirror 2 having an opening in the central portion thereof, a photo-taking lens 3 and a recording medium 4 typified by film in an instant camera or a 35 mm camera or an image pickup element 4 in a television camera through an optical system, not shown, are arranged on an optical path ahead of an eye E to be examined, and an illumination lens 5 and a photographing light source 6 are disposed in the direction of reflection of the apertured mirror 2. In FIG. 1, a camera housing containing the recording medium 4 therein removably mounted on an apparatus body and interchangeable with another one is not shown.

A camera (or a television camera) containing the recording medium therein is designed so as to be capable of outputting data of the kind of the recording medium and the sensitivity of the film contained therein (or the image pickup element) to the connected apparatus body side. The output from the recording medium 4 side is connected to recording medium detecting means 7 for detecting the kind of medium and the sensitivity thereof, and the outputs of this recording medium detecting means 7 and correction selection means 8 of a push button type are connected to a judgment processing portion 9. The correction selection means 8 is designed so as to be capable of inputting a predetermined correction value by means of an increase button or a decrease button. The output of the judgment processing portion 9 is connected to photographing light amount control means 10, the output of which, in turn, is connected to the photographing light source 6.

The kind of recording medium and the sensitivity of the recording medium 4 are detected by the recording medium detecting means 7 and the detection signal is inputted to the judgment processing portion 9. An examiner then depresses the push button of the correction selection means 8 to thereby select a correction value conforming to the kind of recording medium and the sensitivity of the recording medium 4, and this selected correction value is inputted to the judgment processing portion 9. The judgment processing portion 9 converts this correction value into a light amount correction value of an optimum light amount correction width in the recording medium 4, and that value is outputted to the photographing light amount control means 10, which thus causes the photographing light source 6 to emit light on the basis of that value.

The photographing light from the photographing light source 6 illuminates the eye E to be examined through the illumination lens 5, the apertured mirror 2 and the objective lens 1. The reflected light reflected by the eye E to be examined passes through the central portion of the apertured mirror 2 and is introduced as the image of the eye to be examined into the recording medium 4 through the phototaking lens 3 and the optical system, not shown.

Figure 2:
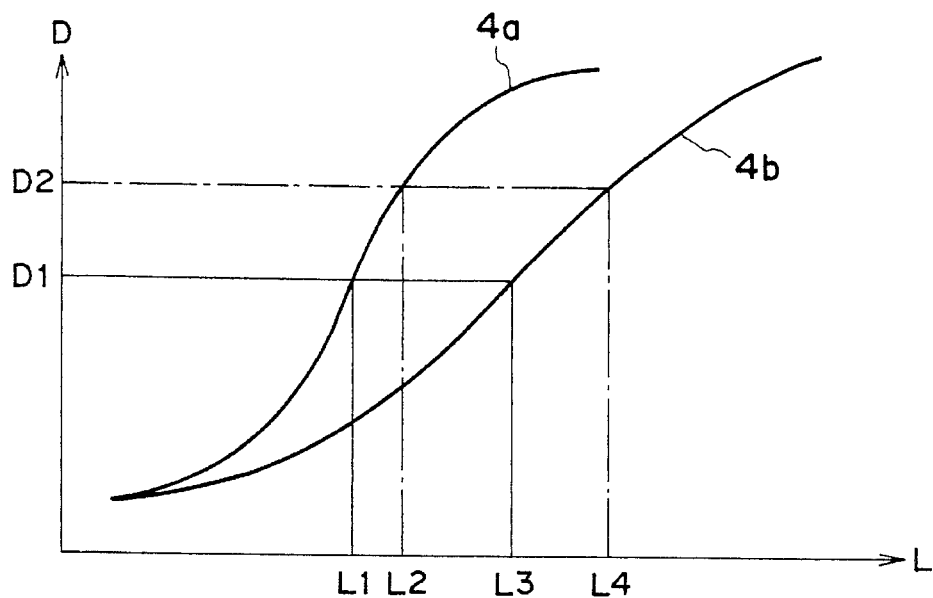
FIG. 2 is a graph showing the relation between the photographing light amount and density of a recording medium.

As regards the recording medium 4, depending on the kind thereof, it is necessary to change the photographing light amount correction width by the correction selection means 8 because, for example, the sensitivity of film used in an instant camera or a 35 mm camera differs. For example, in the case of two kinds of recording media 4 using film of different γ characteristic exhibiting characteristic of the photographing light amount L-density D as shown in FIG. 2, to effect correction from density D1 to density D2 with the density D of the recording medium 4 as the standard, the judgment processing portion 9 sets the light amount correction width to L1–L2 for a certain recording medium 4a and sets the light amount correction width to L3–L4 for another recording medium 4b, whereby it becomes possible to suitably vary the light amount correction width for the recording mediums 4a and 4b differing in γ characteristic to thereby effect light amount correction of an equal density difference. Accordingly, the examiner can always suitable select light amount correction.

Figure 3:
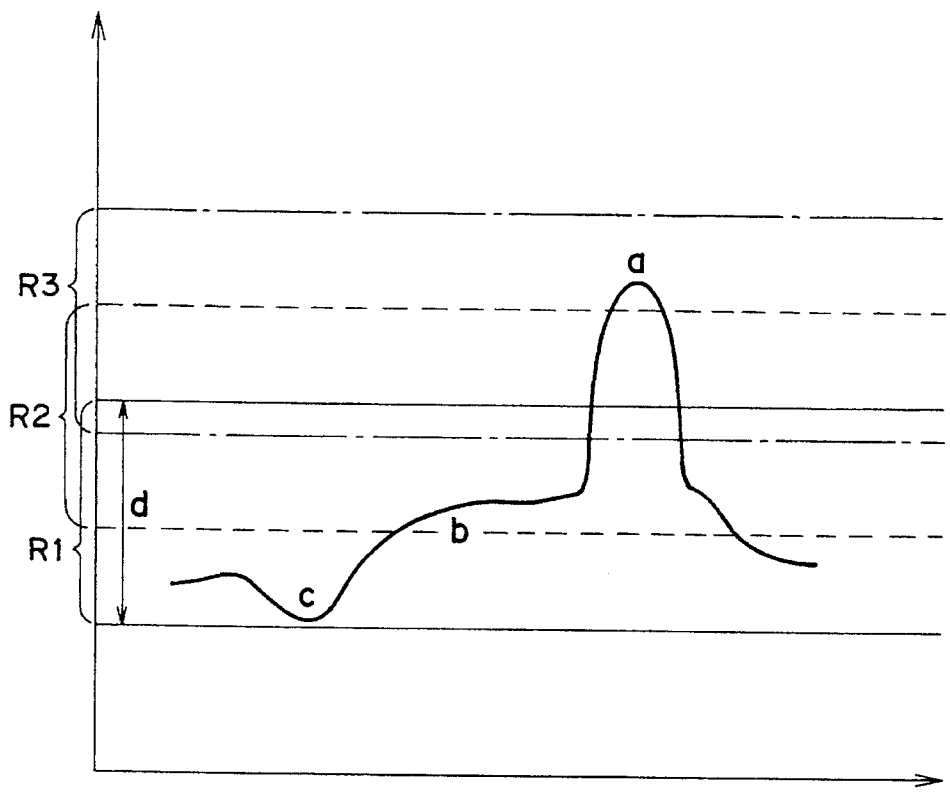
FIG. 3 is a graph showing the reflectance distribution of the fundus of an eye.

Also, when image recording is to be effected by a television camera instead of a camera containing a recording medium therein, it is difficult for the television camera to cover a wide dynamic range with a single image pickup element. That is, when for the distribution of the reflectance R of the fundus of an eye as shown in FIG. 3, use is made of an image pickup element having an ordinary dynamic range d, the range of the reflectance R of the object to be photographed exceeds the dynamic range of the image pickup element and therefore, it becomes impossible to imprint a region a of high reflectance R and a region c of low reflectance R at one time. Further, during actual diagnosis, in order to obtain a good image excellent in linearity, it becomes necessary to adjust the photographing light amount so that the reflectance R of a region to be observed may be in the vicinity of the center of the range.

Accordingly, if for example, regions a, b and c are to be observed, photographing light amount control in a wide range covering the reflectances R of the regions a, b and c becomes necessary. The photographing light amount correction width is preset in conformity with the γ characteristic of the image pickup element. Let it be assumed that for the reflectance R with the region b as the center, the dynamic range in the light amount set at first in which the image pickup element can pick up an image is R1. Assuming that the dynamic range in which the image pickup element can pick up an image when the light amount has been correcting by one stage in conformity with the set photographing light amount width is a range R2 indicated by a broken line, two stages of correction up to a range R3 indicated by a dot-and-dash line becomes necessary to obtain a good image of the region a, and three to four stages of correction becomes necessary to obtain a good image of the whole including the region c. The judgment processing portion 9 prepares a number of photographing light amount correction stages to make up for the wide dynamic range of the image of the fundus of the eye and changes over the number of stages controllable in conformity with the γ characteristic of the image pickup element so that every region of the fundus of the eye can be photographed with an optimum light amount.

In the present embodiment, a single photographing light amount correction selection means 8 is used to vary the photographing light amount correction width or the photographing light amount correction stage, but for example, the photographing light amount correction selection means 8 of FIG. 1 may be used as photographing light amount correction input means, and a plurality of photographing light amount correction input means may be prepared each in conformity with use for respective silver salt film or an image pickup element as indicated by broken lines in FIG. 1, and optimum photographing light amount correction widths for respective recording media or image pickup elements may be preset corresponding to respective light amount correction input means so that the examiner may select one of the photographing light amount correction input means to select the optimum photographing light amount correction width for the medium or element to be used. Likewise, for the plurality of photographing light amount correction input means, optimum photographing light amount correction stages for respective recording media or image pickup elements may be preset corresponding to respective light amount correction input means so that the examiner may select one of them.

Also, in the present embodiment, the photographing light amount correction selection means 8 of a push button type is used, but alternatively, photographing light amount correction input means of a slide type or of a rotational type may be used.

As described above, a provision is made of the detecting means for detecting the kind and/or sensitivity of the recording medium or the image pickup element and the light amount correction means, and by the output of the detecting means, at least one of the optimum photographing light amount correction width and photographing light amount correction stage is set in conformity with the recording medium or the image pickup element, whereby irrespective of the recording medium or the image pickup element, the image of the eye to be examined can always be simply photographed with an optimum exposure.

Also, a provision is made of a plurality of photographing light amount correction input means corresponding to the recording medium or the image pickup element, and at least one of the optimum photographing light amount correction width and photographing light amount correction stage for the recording medium or the image pickup element is preset, whereby the image of the eye to be examined can always be automatically photographed with an optimum exposure amount.

What is claimed is:

1. An ophthalmic photographing apparatus comprising:

photographing means for directing an image of an eye to be examined, obtained by illuminating the eye to be examined with a predetermined photographing light amount, to a recording medium or an image pickup element;

detecting means for detecting information about the kind and/or sensitivity of the recording medium or the image pickup element into which the image of the eye to be examined is introduced;

photographing light amount correction input means for inputting the correction condition of a photographing light amount; and control means for varying at least one of the correction width and the correction stage of the photographing light amount correction condition inputted by said photographing light amount correction input means on the basis of the result of the detection by said detecting means, wherein under the condition that at least one of the correction width and the correction stage is set by said control means, the photographing light amount by said photographing means is controlled on the basis of the input correction condition by said photographing light amount correction input means.

2. The apparatus according to claim 1, wherein said control means varies the correction width of the photographing light amount correction condition in conformity with the detected sensitivity of the recording medium so that the density difference range on the recording medium changeable by the correction width of the photographing light amount which is correctable by said photographing light amount input means becomes constant irrespective of the recording medium.

3. The apparatus according to claim 1, wherein said recording medium is film in an instant camera.

4. The apparatus according to claim 1, wherein said recording medium is film in a 35 mm camera.

5. The apparatus according to claim 1, wherein said control means varies the correction stage of the photographing light amount correction condition in conformity with the detected sensitivity of the image pickup element.

6. An ophthalmic photographing apparatus comprising:

photographing means for directing the image of an eye to be examined obtained by illuminating the eye to be examined with a predetermined photographing light amount to a recording medium or an image pickup element;

detecting means for detecting information about the kind and/or sensitivity of the recording medium or the image pickup element into which the image of the eye to be examined is introduced; and a plurality of photographing light amount correction input means for inputting the correction condition of a photographing light amount, said photographing light amount correction input means being set so that at least one of the correction width and the correction stage of the photographing light amount correction condition differ from the other, wherein a user can select at least one of the correction width and said correction stage by the selection of said photographing light amount correction input means, and the photographing light amount by said photographing means is controlled on the basis of the input correction condition by said selected photographing light amount correction input means.

* * * * *

UNITED STATES PATENT AND TRADEMARK OFFICE
CERTIFICATE OF CORRECTION

PATENT NO. : 5,530,494
DATED : June 25, 1996
INVENTOR(S) : Tetsuji OGAWA, et al.

It is certified that error appears in the above-indentified patent and that said Letters Patent is hereby corrected as shown below:

ON THE COVER PAGE ITEM:

[54] Title of the Invention:

"OPTHALMIC" should read --OPHTHALMIC--.

COLUMN 1:

Line 1, "OPTHALMIC" should read --OPHTHALMIC--.
Line 34, "amount" should be deleted.

COLUMN 3:

Line 23, "mediums" should read --media--.
Line 25, "always" should read --always select a--.
Line 26, "select" should be deleted.

Signed and Sealed this

Fifth Day of November, 1996

Attest:

BRUCE LEHMAN

*Attesting Officer*      *Commissioner of Patents and Trademarks*